US006268530B1

(12) United States Patent
Toth et al.

(10) Patent No.: US 6,268,530 B1
(45) Date of Patent: Jul. 31, 2001

(54) PROCESS TO PREPARE 5-FORMYLVALERIC ACID

(75) Inventors: Imre Toth; Onko Gelling, both of Geleen; Rudolf P. M. Guit, Maastricht; Antonius J. F. Simons, Geleen; Simon Hans H. Niemann, Maastricht, all of (NL)

(73) Assignees: DSM N.V., Heerlen (NL); E. I. DuPont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/030,281

(22) Filed: Jan. 5, 1998

Related U.S. Application Data

(63) Continuation of application No. PCT/NL96/00260, filed on Jun. 26, 1996.

(30) Foreign Application Priority Data

Jul. 4, 1995 (EP) ................................................ 95201814

(51) Int. Cl.⁷ ........................ C07C 59/147; C07D 201/08
(52) U.S. Cl. .......................... 562/577; 562/517; 540/529; 540/538
(58) Field of Search .................................... 562/577, 517; 540/529, 538

(56) References Cited

U.S. PATENT DOCUMENTS

| 2,204,616 | 6/1940 | Othmer ................................. 202/55 |
| 4,730,040 | 3/1988 | Vagt et al. ........................... 540/538 |

OTHER PUBLICATIONS

"CRC Handbook of Chemistry and Physics", 70th edition, 1989–1990 pp. 396–397 Derwent WPI 1963–1999.

Lewis, Hawley's Condensed Chemical Dictionary, Twelfth Edition, p. 1076, 1993.*

* cited by examiner

*Primary Examiner*—Rosalynd Keys
(74) *Attorney, Agent, or Firm*—Pillsbury Winthrop LLP

(57) ABSTRACT

Process to separate linear 5-formylvaleric acid from a mixture of 5- and 3- and 4-formylvaleric acids, wherein the separation is performed by fractional extraction with two immiscible solvents of which one solvent is an aqueous solvent and the other solvent is an organic solvent, in which the organic solvent has a higher or lower affinity for 5-formylvaleric acid than its affinity for the 3-formylvaleric acids and for the 4-formylvaleric acid. Furthermore the invention relates to an improved process to prepare ∈-caprolactam starting from a mixture of branched and linear formylvaleric acids or starting from pentenoic acid.

8 Claims, 2 Drawing Sheets

PROCESS TO PREPARE 5-FORMYLVALERIC ACID

Figure 1:
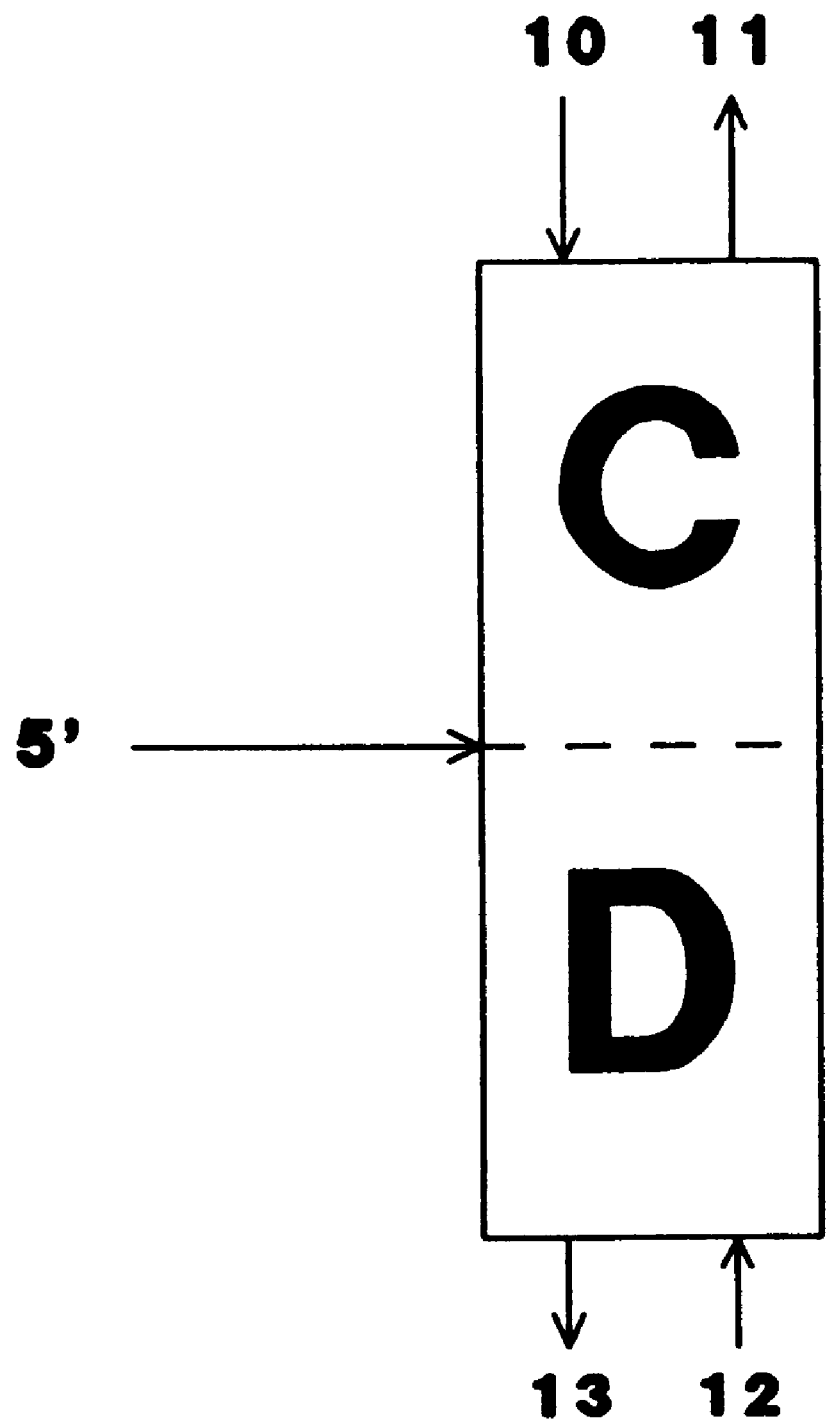

This application claims the benefit of the filing date and a continuation of PCT/NL96/00260, filed Jun. 26, 1996.

The invention relates to a process to separate linear 5-formylvaleric acid from a mixture of 5- and 3- and/or 4-branched formylvaleric acids. The invention also relates to a process to prepare 5-formylvaleric acid starting from pentenoic acid by hydroformylation.

Furthermore the invention relates to an improved process to prepare ∈-caprolactam starting from a mixture of branched and linear formylvaleric acids or starting from pentenoic acid.

It is known from DE-C-952442 that 5-formylvaleric acid can be prepared by hydroformylation of pentenoic acids, for example 3-pentenoic acid. When 5-formylvaleric acid is prepared by hydroformylation branched by-products (3- and/or 4-formylvaleric acid) are also formed. Two methods for separating the linear 5-formylvaleric acid from 3- and 4-formylvaleric acid are described in DE-C-952442: (1) The mixture of branched and linear acids can first be subjected to a reductive amination. The resulting amide product mixture can be separated in linear and branched amide products. (2) The separation of 5- formylvaleric acid from the mixture can be performed by esterification of the linear and branched formylvaleric acids and a subsequent separation of the 5-formylvaleric ester. By hydrolysis of the isolated 5-formylvaleric ester 5-formylvaleric acid can be obtained.

A disadvantage of the first method is that a nitrogen containing waste stream of branched amide products is obtained which is difficult to dispose of. Furthermore, 5-formylvaleric acid is not obtained as an isolated product.

A disadvantage of the second method is that several chemical reactions have to be performed to obtain 5-formylvaleric acid starting from pentenoic acid. Loss of valuable product in these reactions and the need for extra process equipment, and thus an extra investment makes this process unattractive when performed on a large and commercial scale.

The aim of the present invention is to provide a process to separate 5-formylvaleric acid from its isomers, 3- and/or 4-formylvaleric acid, with a high yield to 5-formylvaleric acid in a more simple process than the process described in DE-C-952442.

This aim is accomplished in that the separation is performed by fractional extraction with two immiscible solvents of which one solvent is an aqueous solvent (resulting in an aqueous phase) and the other solvent is an organic solvent (resulting in an organic phase) which has the following characteristics:

$$-2.8 < A < -0.2 \text{ and } 0.14 < B < 2.39 \quad (2)$$

or $$1.7 < A < 4.0 \text{ and } -4.0 < B < -1.64 \quad (3)$$

in which, A and B are:

$$A = 0.23 * (T_B - 138.54)/62.36 + \\
0.24 * (\rho - 935.64)/184.82 + \\
0.0554 * (n_d - 1.4370)/0.0635 + \\
0.3916 * (\epsilon_r - 15.02)/18.66 + \\
0.1208 * (\delta_d - 16.68)/1.738 + \\
0.4135 * (\delta_p - 6.11)/5.16 + \quad (5)$$

$$0.3462 * (\delta_h - 8.05)/6.97 + \\
0.4177 * (\delta - 20.69)/5.087 + \\
0.3370 * (\mu - 1.73)/1.20 + \\
0.3723 * (E_{T(30)} - 41.14)/7.61$$

$$B = -0.3009 * (T_B - 138.54)/62.36 - \\
0.3882 * (\rho - 935.64)/134.82 - \\
0.5914 * (n_d - 1.470)/0.0635 + \\
0.1225 * (\epsilon_r - 15.02)/18.66 - \\
0.5506 * (\delta_d - 16.68)/1.738 + \\
0.0970 * (\delta_p - 6.11)/5.16 + \\
0.2291 * (\delta_h - 8.05)/6.97 + \\
0.0583 * (\delta - 20.69)/5.087 + \\
0.0381 * (\mu - 1.73)/1.20 + \\
0.1550 * (E_{T(30)} - 41.14)/7.61 \quad (6)$$

in which $T_B$ represents the normal boiling point (° C.), $\rho$ the density measured at 20° C. (kg/m³), $n_d$ the refractive index (–), $\epsilon_r$ the dielectric constant measured at 20° C. (–), $\delta_d$ the Hansen solubility parameter of dispersion (MPa$^{1/2}$), $\delta_p$ the Hansen solubility parameter of polarity (MPa$^{1/2}$), $\delta_h$ the Hansen solubility parameter of hydrogen bonding (MPa$^{1/2}$), $\delta$ the Scatchard-Hildebrand solubility parameter (MPa$^{1/2}$), $\mu$ the dipole moment (Debey) and $E_{T(30)}$ the Lewis donor/acceptor property (kcal/mol) (all properties of the organic solvent) or the organic solvent is an ether or an ester with 2 to 10 carbon atoms represented by the following formula

$$R^1—O—R^2 \quad (7)$$

(8)

in which $R^1$, $R^2$, $R^3$ and $R^4$ are independently an alkyl or aryl group with 1 to 7 carbon atoms and in which $R^1$ and $R^2$ is optionally a divalent group.

In this invention it is understood that two solvents are immiscible when two separate phases form when the solvents are mixed.

The values for the above described solvent properties for most of the generally applied solvents can be found in the following references: Properties of liquids and gases, fourth edition, Reid, Prausknitz & Poling, Mc-Graw Hill, 1987; Properties of polymers (Their correlation with chemical structure), D. W. van Krevelen, Elsevier Scientific Publishing Company, Amsterdam 1990; Solvents and Solvent Effects in Organic Chemistry, Ch. Reichardt, VCH Verlagsgesellschaft mbH, Weinheim (Germany, FRG, 1990) and DIPPR—Tables, Physical and thermodynamic properties of pure components, Daubert & Danner, Taylor & Francis, 1994.

It has been found that with the process according to the invention it is possible to separate the linear 5-formylvaleric acid from this mixture with an extraction process. This was unexpected. In particular because the linear and the branched formylvaleric acids have very comparable physical properties. The fact that an extraction process can be used for solving this problem is very advantageous because extraction processes are easily applied in large scale processes.

A further advantage is that it is possible to obtain relatively pure 5-formylvaleric acid in a high yield calculated on the starting amount of 5-formylvaleric acid in the (crude) mixture of formylvaleric acids.

Another advantage is that possible pentenoic acid or valeric acid, can also be separated from the linear 5-formylvaleric acid in the process according to the invention. These compounds are the starting compound and a possible by-product respectively of the hydroformylation process to prepare 5-formylvaleric acid. Thus an additional separation of 5-formylvaleric acid and pentenoic acid and/or valeric acid is not needed if these products are present.

It has been known to prepare 5-formylvaleric acid by hydrolysis of the corresponding methyl 5-formylvaleric as described in U.S Pat. No. 4,730,040. A disadvantage of this process is that methanol is obtained as a by-product and that the yield of the hydrolysis to 5-formylvaleric acid, as shown in the examples of U.S. Pat. No. 4,730,040, is too low for a commercially interesting process. The methyl 5-formylvaleric is preferably prepared by hydroformylation of a methyl pentenoate ester which is preferably prepared by carbonylation of butadiene with methanol. By preparing the pentenoic acid by carbonylation of butadiene with water, followed by the preparation of the formylvaleric acid by hydroformylation of the pentenoic acid the use of methanol or any other alkanol is avoided. Moreover with the present invention it is possible to prepare and isolate 5-formylvaleric acid in less process steps starting from butadiene.

The aqueous solvent used in the process according to the invention may be optionally a mixture of water and another solvent which is miscible with water and has a low solubility in the organic solvent of the other phase such that two separate phases are formed. Preferably water is used as the aqueous solvent.

The organic solvent used in the process according to the invention is characterized with A and B which have values within the A-B space as described by the formula's above or is an ether or ester with formula (7) or (8) respectively.

The organic solvent used in the process according to the invention may be any organic solvent which has a higher or lower affinity for 5-formylvaleric acid (5FVA) than its affinity for both the 3- and the 4-formylvaleric acids (3FVA+ 4FVA). In describing the present invention, it may be useful to use the partition coefficient K as a measure for the above mentioned affinity:

$$K_{acid} = \frac{[acid]_{organic\ phase}}{[acid]_{water\ phase}} \quad (1)$$

in which [acid] is the concentration of the specific formylvaleric acid in the specific phase in moil/1. In order to achieve the benefits of the present invention, the K for 5FVA is smaller or greater than the K for 3FVA and the K for 4FVA. If the K for 5FVA is greater than the K for 3FVA and 4FVA the 5FVA will be obtained dissolved in the organic solvent after the extraction according to the invention. In general the K for 5FVA is smaller and the isolated 5FVA will be obtained in the water solvent after the extraction according to the invention. For practical reasons the K for 5FVA is preferably at least 1.5 times larger or smaller than the average K for 3- and 4FVA.

The organic solvent and water are substantially immiscible. Some quantities of the other solvent will usually dissolve in the other phase in practice. With substantially immiscible is therefore meant that the mutual solubility is not higher than 10 wt %.

Examples of suitable organic solvents are methyl tert-butyl ether, butyl acetate and nitrobenzene. Preferred solvents have a normal boiling point between 30 and 200° C.

It has been found that suitable organic solvents are those solvents which have a similar polarity, polarizability and H-bond formation character as nitrobenzene or more preferably methyl tent-butyl ether (MTBE). Examples of suitable solvents with these similar properties as MTBE are most esters and ethers. Examples of organic solvents which are less suitable, and which do not have a similar polarity, polarizability and H-bond formation character of MTBE or nitrobenzene, are alcohols, for example benzylalcohol, dodecanol, aromatic solvents, such as benzene and toluene, carboxylic acids, such as acetic acid, alkanes, such as n-heptane. However extraordinary alcohols, aromatic solvents and carboxylic acids may be similar to MTBE or nitrobenzene as described above. The qualitative terminology of similar polarity, polarizability and H-bond formation can be quantified with the A- and B-characteristics. Solvents similar to MTBE have A- and B-characteristics according to formula (2). Solvents similar to nitrobenzene have A- and B-characteristics according to formula (3). Preferably in formula (2) and (3):

$$B < -1.12*A + 0.96 \text{ and}$$

$$B > 0.965*A - 1.033 \quad (4)$$

Solvents similar to MTBE have the following characteristics:

$$-2.8 < A < -0.2 \text{ and } 0.14 < B < 2.39 \quad (2)$$

Solvents similar to nitrobenzene have the following characteristics:

$$1.7 < A < 4.0 \text{ and } -4.0 < B < -1.64 \quad (3)$$

Preferably in formula (2) and (3):

$$B < -1.12*A + 0.96 \quad \text{and}$$

$$B > 0.965*A - 1.033 \quad (4)$$

in which, A and B are a function of the solvent properties:

$$
\begin{aligned}
A = &\ 0.23 *(T_B - 138.54)/62.36 + \\
&\ 0.24 * (\rho - 935.64)/184.82 + \\
&\ 0.0554 * (n_d - 1.4370)/0.0635 + \\
&\ 0.3916 * (\epsilon_r - 15.02)/18.66 + \\
&\ 0.1208 * (\delta_d - 16.68)/1.738 + \\
&\ 0.4135 * (\delta_p - 6.11)/5.16 + \\
&\ 0.3462 * (\delta_h - 8.05)/6.97 + \\
&\ 0.4177 * (\delta - 20.69)/5.087 + \\
&\ 0.3370 * (\mu - 1.73)/1.20 + \\
&\ 0.3723 * (E_{T(30)} - 41.14)/7.61
\end{aligned} \quad (5)
$$

$$
\begin{aligned}
B = &\ -0.3009 * (T_B - 138.54)/62.36 - \\
&\ 0.3882 * (\rho - 935.64)/184.82 - \\
&\ 0.5914 * (n_d - 1.470)/0.0635 + \\
&\ 0.1225 * (\epsilon_r - 15.02)/18.66 - \\
&\ 0.5506 * (\delta_d - 16.68)/1.738 + \\
&\ 0.0970 * (\delta_p - 6.11)/5.16 + \\
&\ 0.2291 * (\delta_h - 8.05)/6.97 + \\
&\ 0.0583 * (\delta - 20.69)/5.087 +
\end{aligned} \quad (6)
$$

Examples of organic solvents which are within the A-B space as described by the formula's above are (solvent (A,B)), methyl tert-butyl ether (−2.2, 1.7), butylacetate (−1.09, 0.62), nitrobenzene (2.09, −2.08), di-ethylether (−2.42, 2.01), ethyl tert-butyl ether (−2.13, 1.51), methyl acetate (0.82, 1.38), ethyl acetate (−1.01, 1.06), di-ethylketone (0.39, 1.01) or di-isopropylketone (−0.97, 0.72).

Typical examples of less suitable solvents are benzylalcohol (1.53, −1.65), dodecanol (0.11, −0.44), benzene (−2.17, −1.36), toluene (−1.95, −1.29), n-heptane (−3.2, 0.83). The A and B values of these less suitable solvents fall outside the ranges of the above formula's.

As mentioned before another group of suitable organic solvents are ethers and esters with 2 to 10 carbon atoms which can be represented by the formula (7) and (8) respectively.

This group of ethers and esters is not necessarily restricted to the A-B space as described above. Preferably at least $R^1$ in the ether compound with formula (7) is an alkyl group. Preferably at least $R^3$ or $R^4$ is an alkyl group in the ester compound with formula (8). Examples of ethers are methyl tert-butyl ether, ethyl tert-butyl ether, diethylether, diisopropylether, dibutylether, dipropylether, anisol or tetrahydrofurane. Examples of possible esters are butyl acetate, propylacetate, ethylacetate, methylacetate, ethylbutyrate, methylbutyrate, methylpropionate, methylpropionate or propylpropionate.

Ethers are preferred over esters because esters can transesterify with the formylvaleric acid in which mixed esters are formed which is disadvantageous.

FIG. 1 is a schematic representation of a fractional extraction performed in a gravity separated extractor as will be further described below.

Figure 2:
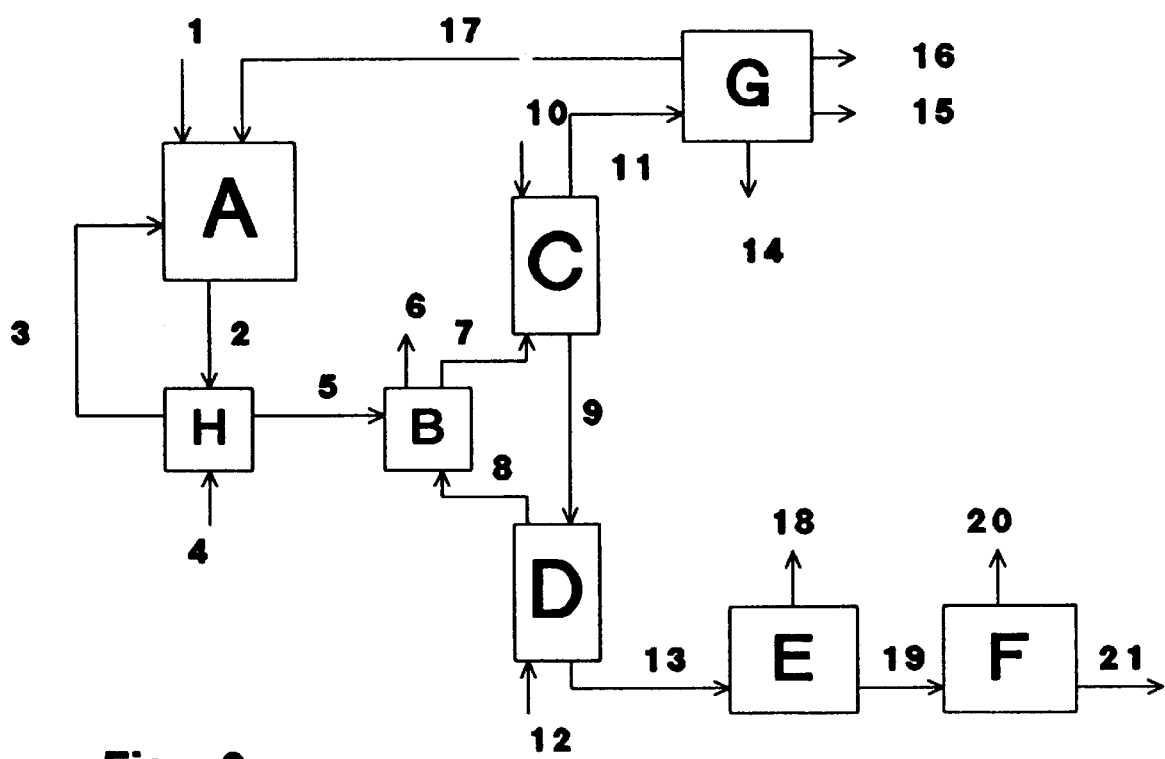

FIG. 2 is a schematic representation of a process in which pentenoic acid is converted in several steps to P-caprolactam comprising a hydroformylation section (A+H) an extraction process according to the invention (C+D+optionally B) combined with an upgrading section (G+E) and a caprolactam-end section (F). The combination of these sections in this figure is not meant to limit the present invention to this integral process for the preparation of ∈-caprolactam.

The separation of 5-formylvaleric acid from the crude mixture of formylvaleric acids is performed by a fractional extraction according to the invention. In general, this fractional extraction merely involves the intimate contact of an impure material with both phases of the fractional extraction, which phases are substantially immiscible, such that the impurities are preferentially dissolved in one of the phases and the material being purified (5FVA) is dissolved in the other phase. Preferably the initial aqueous and organic solvent are used in a substantially pure form. With pure form is meant that no or almost no formylvaleric acids are present. The material being purified is then recovered from solution in its particular phase. The recovered 5FVA product will contain less 3FVA and 4FVA impurities than the crude mixture. The process can be performed discontinuously but is preferably performed continuously.

The extraction performance can be further improved by using an extraction enhancing agent. Examples of these agents are bases or complexing agents. In the process of the present invention the separation can however be performed without using these agents. By leaving out these enhancing agents a more simple process is obtained.

The temperature and pressure at which the fractional extraction is performed is not critical. In general the next ranges are suitable. The pressure of the extraction is preferably between 0.1 and 0.5 MPa. The temperature of the extraction is preferably between 20° and 100° C. Generally the temperature is lower than the boiling point of the organic solvent at the used pressure.

Any of the known methods for accomplishing a fractional extraction with two solvents may be utilized to carry out the present invention. For example, mixer-settlers settlers may be used where crude formylvaleric acid mixture is merely added to a vessel containing both solvent phases of the fractional extraction system and then the mixture is agitated vigorously to accomplish intimate contact of the crude formylvaleric acids with each of the two solvent phases. One of the solvents can contain the crude formylvaleric acids. After sufficient mixing, the phases are allowed settle out through gravity or through the use of a centrifuge.

If both a high purity and high yield of formylvaleric acid is required the process according to the invention is preferably performed continuously in which the mixture of formylvaleric acids is contacted with the two extraction solvents in a plurality of contacting stages.

Such a continuous process is characterized in that continuously the initially aqueous solvent and initially pure organic solvent are contacted counter currently in various contacting stages in which the crude mixture of formylvaleric acids is continuously fed at an intermediate stage.

An example of a preferred continuous fractional extraction is accomplished in a gravity separated extractor comprising some sort of vertical column (see also FIG. 1) which generally contains packing, baffles or trays in order to increase the efficiency of the extraction. In using such columns the crude formylvaleric acids will preferably be fed to the column at a midpoint thereof (5') while the pure (heavy) aqueous phase will be fed to an upper point in the column (10) and above the feed point of the crude formylvaleric acids. The pure (lighter) organic solvent phase will be fed to a lower point in the column (12) and below the feed point of the crude formylvaleric acids. By force of gravity the lighter phase will migrate countercurrently upwardly dissolving the branched formylvaleric acids (in case the K of 5FVA is smaller than the K of 3FVA and 4FVA. This situation shall also be discussed below) and will be removed overhead (11). The heavier phase will migrate downwardly through the column dissolving the 5-formylvaleric acid and will be removed as bottoms from the column (13).

The gravity separated extractor is normally a cascade like apparatus (C+D). The feed point of the crude formylvaleric acid divides the cascade in an enriching section (D) and in a stripping section (C) (the letters and numbers refer to apparatus and streams as described in FIGS. 1 and 2).

The enriching section (D) is generally a vertically placed extraction column with between 5 and 100 and preferably between 10 and 40 theoretical separation stages. The stripping section (C) is also generally a vertically placed extraction column with between 5 and 100 and preferably between 10 and 40 theoretical separation stages. The two sections may form one column or may be split in two (or more) columns.

The crude mixture formylvaleric acid can be in a liquid form as such or dissolved in a solvent. Normally this solvent is water or the organic solvent which is used in the fractional extraction. In a continuous process using a gravity separator the concentration of the crude formylvaleric acids in the feed is preferably between 20 and 100 weight percentage. A lower concentration will generally result in economically unattractive dimensions of the stripping (C) and enriching (D) sections.

Preferably the concentration of formylvaleric acids is as high as possible (provided phase separation at the feed point still occurs) at the feed point (plate) in the gravity separated extraction column. To accomplish this optimal formylvaleric acid concentration, which is for example around 50–60 weight % when MTBE is used as organic solvent, it can be useful to separate some of the solvent present in the feed or solvent leaving the enrichment section and before entering the stripping section. The concentration of formylvaleric acids at the feed point (plate) is the average concentration of streams (7) and (9). An example of such solvent separation is given in FIG. 2: In separator B organic solvent of stream (8) leaving the enrichment section and organic solvent of the feed (5) is separated (6) and the concentrated mixture (7) is fed to the stripping section (C).

The solvent separation in (B) can for example be performed in one flash or simple distillation step at a pressure of between 0.1 and 0.5 MPa.

The aqueous and organic solvent volume flow rates defined by the following formula's $$1/K_{SFVA}*[10]/[7] \quad (9)$$

and $$K_{3FVA}*[12]/[9] \quad (10)$$

and $$K_{4FVA}*[12]/[9] \quad (11)$$

are preferably larger than 1 and more preferably between 1.1 and 2, in which [10], [7], [12] and [9] are the respective volumetric flow rates of the water and organic solvent phases entering the stripping and enrichment sections corresponding with flows (10), (7), (12) and (9) (as shown in FIG. 2).

The lighter organic phase obtained overhead (11) can be further processed in order to obtain substantially purified organic solvent (14) and branched formylvaleric acid (15). When the crude mixture is obtained in a hydroformylation of pentenoic acid, valeric acid and/or pentenoic acid are also obtained overhead. The purified organic solvent (14) can be recycled to the fractional extraction column (10). The organic solvent (14), the branched formylvaleric acid (15), unconverted pentenoic acid (17) and valeric acid and other byproducts (16) of the hydroformylation can be obtained in separate flows by for example distillation. The branched formylvaleric acids may be further processed, for example by a decarbonylation, in which the starting compound of the hydroformylation, pentenoic acid, is obtained. The unconverted pentenoic acid can advantageously be used as starting compound (17) in a hydroformylation (A) to prepare 5-formylvaleric acid. The aqueous phase (13), rich in 5-formylvalexic acid, leaving the enrichment section (D) can be further processed, so that substantially pure 5-formylvaleric acid is obtained. For example, 5-formylvaleric acid can be separated from the mixture by crystallization or more preferably by distillation or extraction with an organic solvent. This organic solvent can for example be the organic solvent used in the dual solvent extraction, but also other organic solvents may be used. Examples of other suitable solvents are benzene, toluene or xylene.

The linear 5-formylvaleric acid can be advantageously used as starting compound for the preparation of adipic acid by (quantitative) oxidation. Adipic acid is an Nylon-6.6 intermediate.

Another example of a very interesting use is the reductive amination of the 5-formylvaleric acid to 6-aminocaproic acid and the subsequent cyclization to ∈-caprolactam. The 5-formylvaleric acid is preferably obtained by hydroformylation of pentenoic acid to a mixture of 3-and/or 4- and 5-formylvaleric acid and subsequently separating 5-formylvaleric acid from 3- and/or 4-formylvaleric acid with the process according to the invention. ∈-caprolactam is a precursor for nylon-6. The reductive amination of 5-formylvaleric acid and the cyclization to ∈-caprolactam is for example described in the above mentioned DE-C-952442 and U.S. Pat. No. 4,730,040. The reductive amination may be performed in any suitable solvent in which the 5-formylvaleric acid is soluble. Examples of these solvents are water, ammonia, $C_1$–$C_6$ alkanols, for example methanol, ethanol, propanol or butanol, ethers, for example diethyl ether, methyl tert-butyl ether, dipropylether or diisopropylether. Ethers are solvents because 5-formylvaleric acid can be easily extracted from the aqueous phase with an ether. More, preferred water is used as the solvent because the 5-formylvaleric acid is obtained dissolved in water after the fractional extraction. Optionally part of this water (18) is separated from the aqueous mixture before the reductive amination. Preferably this separation of water is performed by distillation, and more preferably by effect evaporation. In an effect evaporation water is separated in two or more units in which each unit is operated at a lower pressure than the prior unit and in which the evaporated water (steam) of a prior unit is condensed in a further unit, thereby supplying the heat necessary to evaporate water in the further unit.

With reductive amination is meant the reaction of the 5-formylvaleric acid with a molar excess of ammonia and hydrogen. The reductive amination is generally performed in the presence of a group 8–10 metal containing (hydrogenation) catalyst, for example Ni, Co, Ru, Pt or Pd. Examples of specific hydrogenation catalysts are Raneynickel, Raney cobalt and supported Ru catalysts for example Ru on carbon or Ru on alumina. Ammonia is present in a 2 to 50 fold molar excess. The pressure is super atmospheric, preferably between 0.5 and 30 MPa. The temperature is generally between 40 and 150° C. The catalyst may for example be present as a slurry or fixed in a packed bed. The reductive amination may for example be performed in a tube reactor or a continuously stirred tank reactor.

The cyclization is preferably performed in the same aqueous mixture as used in the reductive amination. Other possible solvents are $C_1$–$C_6$ alkanols. The cyclization is carried out in a separate step after the reductive amination. Preferably the catalyst of the reductive amination is not present during the cyclization. The temperature of the cyclization step is generally between 150 and 370° C. and preferably above 260° C. The cyclization may for example be performed in a tube reactor or in a continuously stirred tank reactor. After cyclization of 6-aminocaproic acid to ∈-caprolactam the ∈-caprolactam (21) and water (20) can be separated by for example crystallization or preferably distillation or extraction.

The crude mixture containing linear and branched formylvaleric acids can be, for example, obtained by hydroformylation of a pentenoic acid. The hydroformylation reaction, in which the pentenoic acid reacts with carbon monoxide and hydrogen, will in general/preferably be performed in the presence of a homogeneous catalyst system. However heterogeneous hydroformylation catalyst systems may also be used. The catalyst system will comprise a Group VIII metal of the Periodic Table of Elements. Preferred metals are Co, Ru, Rh, Pd, Ir and Pt. In DE-A-3628664 a Rh-triphenylphosphine catalyst system is described for the preparation of formylcarboxylic acids by hydroformylation. For the specific preparation of formylcarboxylic acids and especially 5-formylvaleric acid by hydroformylation not many catalyst systems are described in literature. However the known catalyst systems for hydroformylation in general, based on the above described metals are in most cases suitable for this reaction.

Preferred hydroformylation processes to prepare 5-formylvaleric acid are performed in an aqueous reaction mixture, because the pentenoic acid dissolves well in such an aqueous mixture. When performing the reaction in an aqueous reaction mixture the starting compound may also be a pentenoate ester. The ester group will—during the hydroformylation reaction—undergo hydrolysis to the acid group by which the formylvaleric acid will be formed. Preferably the catalyst systems of these processes have a greater solubility in water than the branched and linear formylvaleric acids when extracted with a suitable solvent. This is advantageous because the catalyst system can then be easily separated from the crude formylvaleric acids by extraction (H). Preferably the extraction is performed with the same organic solvent as used in the fractional extraction in the process according to the invention. The aqueous mixture still containing the catalyst system (3) also obtained in such an extraction (H) can be advantageously recycled to the hydroformylation (A).

An example of such a catalyst system is a rhodium based catalyst system combined with water soluble bidentate phosphine ligands. Such a catalyst system is for example described in WO-A-9426688.

Preferably a catalyst system is used comprising platinum or a platinum compound and a water soluble organic bidentate ligand. It has been found that, apart from the above mentioned advantages, a hydroformylation process using such a catalyst system will result in a high selectivity to the linear 5-formylvaleric acid.

Preferably, the water-soluble compound used as bidentate ligand may be represented by the following general formula:

$$-R^5-R^6-M^1-R-M^2-R^7R^8 \qquad (12)$$

where $M^1$ and $M^2$ represent a phosphorus (P) atom, an antimony atom or an arsenic atom, R represents a divalent organic bridging group having at least three atoms and where $R^5$, $R^6$, $R^7$ and $R^8$ represent the same or different organic groups and where $R^5$, $R^6$, $R^7$, $R^8$ and/or R comprise at least one hydrophilic group. It is preferred for $M^1$ and $M^2$ to be phosphorus (P) atoms.

The hydrophilic group may be any group which increases the solubility of the organic bidentate ligand in water. This hydrophilic group may be a strongly polar group, for example amine derivatives, for example dialkylamine groups or more preferably a ionic group. The position of the hydrophilic group in the ligand compound is not critical. The hydrophilic group may be linked to the groups $R^5$–$R^8$ or to the bridging group R.

Examples of suitable ionic hydrophilic groups are a sulphonate group, —$SO_3Z$, a phosphonate group, —$PO_3Z$, a carboxylate group, —COOZ, or a monovalent cationic group of an ammonium salt —$N(R^9)_3X$, where Z represents a monovalent cationic group, $R^5$ an aliphatic or aromatic hydrocarbon group having from 1 to 18 carbon atoms or hydrogen and X represents an anionic group. If the bidentate ligand contains aryl groups, for example for $R^5$, $R^6$, $R^7$ and/or $R^8$, the cationic group of an ammonium salt preferably is bonded to a non-aryl group in the bidentate ligand. These non-aryl groups can be the bridging group (R) or the non-aryl groups for $R^5$–$R^8$. Another example of a hydrophilic group is a phenolate group Ar—OZ, present in the ligand. The Ar group may be any (aromatic) group $R^5$, $R^6$, $R^7$, R8 and/or R.

Examples of suitable cationic groups (Z) are the inorganic cations of metals, especially of alkali and earth alkali metals, for example sodium, potassium, calcium and barium as well as quaternary ammonium ions, for example tetramethylammonium, tetrapropylammonium or tetrabutylammonium.

Examples of suitable anionic groups (X) are halides, sulfate and phosphate groups and $R^{10}$—$SO_3$—, $R^{10}$—$CO_2$ and $R^{10}$—$PO_3$— groups, where $R^{10}$ represents a $C_1$–$C_{12}$ alkyl or $C_1$–$C_{12}$ aryl.

In general, the number of hydrophilic groups is between 1 and 6. It is preferred for the number of groups to be between 1 and 4 per molecule of bidentate ligand.

$R^5$, $R^6$, $R^7$ and $R^8$ may be $C_1$–$C_{15}$ (cyclo) alkyl groups or $C_5$–$C_{20}$ aryl groups. These groups preferably are aryl groups such as naphthyl, phenyl or a heterocyclic aryl group such as pyridyl. Examples of possible substituents are alkyl groups, for instance a methyl, ethyl orisobutyl group, alkoxy groups, for instance methoxy, ethoxy, isopropoxy and halides.

Bridging group R may be an organic group with 3–30 carbon atoms. R may be a divalent $C_9$–$C_{12}$ alkyl group, for example trimethylene, tetramethylene, pentamethylene or hexamethylene.

Examples of bidentate phosphine ligand compounds according to formula (9) without the hydrophilic group are 1,3-bis(diphenyl-phosphino)propane, 1,4-bis (diphenyl-phosphino)butane, 2,3-dimethyl-1,4- bis (diphenylphosphino)butane, 1,4-bis (dicyclohexylphosphino)butane, 1,3- bis(di-p-tolyl-phosphino) propane, 1,4-bis(di-p-methoxyphenylphosphino)butane, 2,3- bis (diphenylphosphino) 2-butene, 1,3-bis(diphenylphosphino)-2-oxopropane and 2-methyl-2(methyldiphenylphosphino)-1,3-di (diphenylphosphino)propane. The above ligands, when substituted with one or more hydrophilic group, are examples of possible water soluble bidentate ligand compounds used in the process according to the invention.

Preferably the bridging group R forms a "rigid" link between $M^1$ and $M^2$. By a "rigid" link is meant a link that allows $M^1$ and $M^2$ little or no conformational freedom relative to one another (comparable to a double bond, which also allows little conformational freedom) irrespective of which groups $R^5$–$R^8$ are present. It has been found that bidentate phosphine ligand compounds having a bridging group that allows more conformational freedom yield less favorable results. Preferably the shortest distance between $M^1$ and $M^2$ is formed by 3, 4 or 5 atoms. These atoms may represent, besides carbon, a heteroatom such as the nitrogen, oxygen, sulfur and phosphor atoms.

Example of suitable "rigid" bridging groups are divalent organic groups containing at least one cyclic group in the chain between $M^1$ and $M^2$, which cyclic group may be aromatic. This cyclic group imparts the "rigid" properties to the bridging group and may possibly be linked to $M^1$ and/or $M^2$ via an alkyl group having from 1 to 3 carbon atoms. An example of suitable bridging groups may be represented by the following general formula:

$$-R^{11}-Y-R^{12}- \qquad (13)$$

where Y represents a hydrocarbon group, which group contains at least one cyclic structure (which cyclic structure imparts rigidity to the bridge group), the cyclic structure optionally being substituted and which hydrocarbon compound may contain heteroatoms such as oxygen, nitrogen, phosphorus and sulfur and where $R^{11}$ and $R^{12}$ may independently of one another be omitted or may independently of one another represent a $C_1$–$C_3$ alkylene group preferably, the cyclic structure will contain from 3 to 20 atoms. $M^1$ and $M^2$ may be cis or trans to the rigid ring Y. If a group $R^{11}$ and/or $R^{12}$ is/are present, it/they, too, may be cis or trans to the rigid bridge Y.

An example of a bidentate phosphine having a cyclic structure in Y which contains a heteroatom is 2,3-o-isopropylidene-2,3-dihydroxy-1,4-bis(diphenylphosphino) butane (DIOP), which is commercially available. Compounds derived from DIOP are also suitable. Another group of cyclic structures for Y in formula (13) are cyclic alkanes such as cyclopropane, cyclobutane, cyclopentane and cyclohexane. Bridged cycloalkanes, too, are highly suitable to be used as cyclic group Y in formula (13). Examples of such bridged cycloalkanes are bicyclo [1,1,2]hexane, bicyclo [2,2,1]heptane and bicyclo [2,2,2]octane.

The cyclic structure of Y may optionally be substituted with one or more aryl or alkyl groups and/or with other functional groups. The functional groups substituted on Y may also be hydrophilic groups which increases the solubility of the organic bidentate ligand used in the process according to the invention. The functional groups may optionally be used for immobilizing the bidentate phosphine on a carrier. Examples of these functional groups are, for instance, carbonyl, hydroxyl, amine and halide groups.

Other suitable "rigid" bridging groups are divalent organic groups containing (at least) 2 coupled, preferably aromatic, ring systems. The two ring systems have a hindered rotation relative to one another, as a result of which the bridges possess 'rigid' properties. Such compounds are described in detail in, for instance, "Advanced Organic Chemistry, Reactions, Mechanisms and Structure", Jerry March, 4th ed. 1992, John Wiley & Sons, page 101. Examples of suitable coupled ring systems are biphenyl, binaphthyl and bipyridyl. An example of a bidentate phosphine with a "rigid" bridge group with coupled ring systems is 2,2'-bis-(diphenylphosphino)-1,1'binaphthyl (BINAP), which is commercially available. The ring systems may be substituted in the same way as the cyclic structure Y described above.

A completely different group of suitable "rigid" bridging groups R with cyclic compounds are bis($\eta$-cyclopentadienyl)—coordination compounds of metals (also known as metallocenes). A particularly suitable metallocene is ferrocene.

Examples of suitable bidentate phosphines with rigid bridging groups (R) into which hydrophilic groups have not yet been incorporated are the earlier mentioned DIOP, bis(diphenylphosphine)ferrocene, trans-1,2-bis(di(m-methylphenyl)phosphinomethyl)cyclobutane, trans-[(bicyclo[2.2.1]heptane-2,3-diyl)bis(methylene)]-bis [diphenylphosphine], trans-[(bicyclo[2.2.2]octane-2,3-diyl) bis(methylene)]-bis[diphenylphosphine], trans- 1,2-bis (diphenylphosphinomethyl)cyclobutane(DPMCB), trans-1, 2-bis[diphenylphosphinomethyl]trans-3,4bis[phenyl] cyclobutane and the earlier mentioned BINAP.

The hydrophilic groups can readily be linked to the above-mentioned compounds. Sulfonate groups, for instance, can be bonded to the ligand via sulfonation with the aid of $SO_3$ in sulfuric acid. Carboxylate groups, phosphonate groups and cationic radicals of an ammonium salt can be incorporated using synthesis processes known in the art.

Platinum or the platinum compound can be applied in a homogeneous system or a heterogeneous, immobilized system. Homogeneous systems are preferred. Since platinum forms a complex with the bidentate compound in situ, the choice of an initial Pt compound is not generally critical. Suitable platinum compounds are for example salts of platinum with, for instance, hydrogen halides, nitric acid, sulfonic acid and carboxylic acids having not more than 12 carbon atoms per molecule. Examples of such salts are $PtCl_2$,$Pt(AcAc)_2$ (AcAc=acetylacetonate), $CODPtCl_2$ (COD=cyclooctadiene), $Pt(CH_3CN)_4(BF_4)_2$ and CODPt (AcAc) $BF_4$.

The temperature of the hydroformylation is in general between 50 and 200° C. and preferably between 90 and 120° C.

The pressure is not critical and may e.g. be between 4 and 20 MPa.

The molar ratio of hydrogen to carbon monoxide may e.g. be between 1:10 and 10:1. This ratio affects the ratio of the yield of formyl carboxylic acids to the yield of dicarboxylic acids. The dicarboxylic acids content of the resulting reaction mixture will increase as more carbon monoxide is used. If the desired product is formyl carboxylic acid, the molar ratio of carbon monoxide to hydrogen will be about 1:1. If a significant amount of dicarboxylic acids is desired, the molar excess of carbon monoxide relative to hydrogen is higher than 5.

The molar ratio of unsaturated carboxylic acid to platinum as a rule is between 100:1 and 1000:1 but preferably between 400:1 and 600:1.

The molar ratio of unsaturated carboxylic acid and water as a rule lies between 1:20 and 1:2.

Next to water other solvents may optionally be present. Examples of other solvents are dimethylformamide, tetrahydrofuran, benzonitril and acetonitril.

Pentenoic acid used as starting compound for the above hydroformylation can be 4-, 3- or 2-pentenoic acid or mixtures of these compounds. Pentenoic acid can advantageously be prepared by carbonylation of butadiene and water as for example described in EP-A-405433.

As explained before the water obtained in the extraction (18) and ∈-caprolactam preparation (20) can be advantageously be reused in the extraction (10) and cyclization (22). The organic solvent obtained in the extraction (6) and (14) can be advantageously be reused in the hydroformylation extraction (4) and (12). Optionally these streams can be subjected to an additional purification.

The invention will be elucidated with the following non-limiting examples.

Examples IA–Ib and comparative Experiment A were performed with methyl tert-butyl ether, butylacetate and toluene.

For the calculation of their A and B's the following solvent properties were used:

| | UNIT | MTBE | BUTYL-ACETATE | TOLUENE |
|---|---|---|---|---|
| $T_b$ | ° C. | 56 | 126 | 110 |
| $\rho$ | $Kg/m^3$ | 745 | 876.1 | 867 |
| $n_d$ | — | 1.37 | 1.39 | 1.50 |
| $\epsilon_r$ | — | 3.672 | 6.0 | 2.379 |
| $\delta_d$ | MPa½ | 14.5 | 15.8 | 18.0 |
| $\delta_p$ | MPa½ | 2.9 | 3.7 | 1.4 |
| $\delta_h$ | MPa½ | 5.1 | 6.3 | 2.0 |
| $\delta$ | MPa½ | 15.8 | 17.4 | 18.2 |
| $\mu$ | Debye | 1.28 | 1.84 | 0.31 |
| $E_{T(30)}$ | Kcal/mol | 35.5 | 38.0 | 33.9 |
| A | — | −2.21 | −1.09 | −1.95 |
| B | — | 1.70 | 0.62 | −1.28 |

EXAMPLE Ia

A mixture of 2.25 g 5-formylvaleric acid (17 mmol), 0.21 g 3-formylvaleric acid (1.6 mmol) and 0.50 g 4-formylvaleric acid (3.8 mmol), 0.86 g pentenoic acid (8.6 mmol), 0.7 g valeric acid (6.8 mmol) and 47 g water in which the mixture had a total volume of 50 ml, was contacted at 22° C. with 50 ml methyl tert-butyl ether (MTBE) for 2 minutes. The two phases were separated by phase separation and analyzed by gas chromatography.

|  | water | MTBE |  |
| --- | --- | --- | --- |
| 5-formylvaleric acid[1] | 50% | 50% | (= 100%) |
| 3-formylvaleric acid | 35 | 65 |  |
| 4-formylvaleric acid | 36 | 64 |  |
| 3-pentenoic acid | 13 | 87 |  |
| valeric acid | 12 | 88 |  |

[1] percentage of the original amount in the respective phases.

EXAMPLE Ib

Example Ia was repeated with the same weight amount of butylacetate instead of MTBE:

|  | Water | Butylacetate |  |
| --- | --- | --- | --- |
| 5-formylvaleric acid | 48 | 52 | (= 100%) |
| 3-formylvaleric acid | 31 | 69 |  |
| 4-formylvaleric acid | 31 | 69 |  |
| 3-pentenoic acid | 4 | 96 |  |
| valeric acid | 5 | 95 |  |

Comparative Experiment A

Example I was repeated with toluene instead of MTBE. The results were:

|  | water | toluene |  |
| --- | --- | --- | --- |
| 5-formylvaleric acid | 87 | 13 | (= 100%) |
| 3-formylvaleric acid | 87 | 13 |  |
| 4-formylvaleric acid | 85 | 15 |  |
| 3-pentenoic acid | 16 | 84 |  |
| valeric acid | 15 | 85 |  |

As is clear from Examples Ia, Ib and comparative experiment A, the use of toluene does not result in a separation of the 5-formylvaleric acid from the 3- and 4 formylvaleric acid, and that separation activity is observed when MTBE and butylacetate are used as organic solvent. Furthermore, these experiments show that in order to obtain substantially pure 5-formylvaleric acid, several extraction stages are necessary. Therefore, it appears advantageous, to perform the invention in a continuous multi stage extraction.

EXAMPLE III

The following were weighed into a 150-ml Hastalloy C autoclave: 37.4 mg (0.1 mmol) of CODPtCl$_2$(COD=1,5-cyclooctadiene) and 89.7 mg (0.1 mmol) of tetrasulfonated trans-1,2-bis(diphenylphosphino-methylene)cyclobutane in 45 ml of degassed water. After half an hour of stirring, 5.3 g of freshly distilled 3-pentenoic acid was added and the autoclave was heated to 100° C. at 5.0 MPa with CO/H$_2$=1 (mol/mol). The final pressure was adjusted to 8.0 MPa with the CO/H$_2$ gas mixture. After 4 hours the reaction mixture was cooled. The pressure was relieved after the reaction mixture had cooled down. The aqueous reaction mixture was then extracted with MTBE (3×50 ml) under a nitrogen atmosphere. After this first cycle the ether phase was analyzed by GC. The amounts of products and starting materials in the ether layer are given in Table 1. Hereafter, an amount of fresh 3-pentenoic acid was added to the aqueous phase (Table 1, column 1), whereupon the reaction was repeated in the manner described above. This cycle was repeated five times. The etheral extract was analyzed by GC after each cycle. After the last cycle the water phase was also analyzed by GC. Table 1 shows the amounts of 3-pentenoic acid and the results of each cycle. These results indicate that the catalyst can readily be reused while retaining its activity.

The total conversion after 4 cycles was 78.8%. The selectivity for valeric acid was 6.2%, for 5-formylvaleric acid 62%, for total formylvaleric acids 80.3%, for dicarboxylic acids 11.4%. N/Br was 3.4.

EXAMPLE IV

In a laboratory a glass pilor column, 0.05 m in diameter and 4.5 m in height, was modified so as to accomplish a fractional extraction separation of 5FVA from 3- and 5-formylvaleric acids:

An inlet point for the crude formylvaleric acid was placed about 3 m from the bottom of the glass column, an inlet for a fresh MTBE stream provided about 0.20 m from the bottom of the column and an inlet for water provided about 0.20 m from the top of the column. The bottom of the glass column itself was adapted for removal of the aqueous phase and the top of the column fitted for removal of the MTBE phase.

The column as packed with 12 mm ceramic Raschig rings. To be able to control the interfacial mass-transfer area a pulsator was attached to the bottom of the column to generate an up and down movement of the total liquid content of the glass column. Both the amplitude and the frequency of the pulsation could be varied as a means of controlling the energy dissipation in the extraction column.

An acid mixture as obtained in Example III, consisting of 3.25 kg/h MTBE, 1.17 kg/h 5FVA, a total of 1.40 kg/h 3- and 4-formylvaleric acids, 0.23 kg/h pentenoic acid and 0.46 kg/h dicarboxylic acids, the pure MTBE and the pure water were fed continuously to the column at the points referred to above; the flow rate of pure water equaled 16.25 kg/h and the flow rate of pure MTBE equaled 6.97 kg/h. During the operations the feed streams as well as the column were maintained at about 25° C. The frequency and stroke length of pulsation were set to 90 strokes per minute and 0.01 m, respectively.

Both the organic top stream and the aqueous bottom stream were analyzed for the different acids. The weight ratio of the 5FVA to the total amounts of acids in the aqueous bottom stream (the purity of the 5FVA) was about 0.98 (the other components were 3FVA and 4FVA) and the yield of 5FVA (the mass-flow rate of 5FVA in the aqueous bottom stream relative to the mass-flow rate of 5FVA in the acid feed) was about 0.98.

TABLE 1

| 3-PA added (g) (1) | cycle | PA-s (g) (2) | VA (gPa) (3) | 5-FVA (gPa) (4) | FVA (gPa) (5) | dicarboxylic acids (gPa) (6) | rest (gPa) | total (gPa) | ToF (7) |
|---|---|---|---|---|---|---|---|---|---|
| 5.30 | 1 | 1.16 | 0.25 | 1.85 | 2.51 | 0.34 | 0.04 | 4.30 | 103.3 |
| 4.84 | 2 | 0.70 | 0.25 | 2.38 | 3.11 | 0.51 | 0.05 | 4.62 | 103.3 |
| 4.97 | 3 | 0.76 | 0.26 | 2.72 | 3.52 | 0.52 | 0.10 | 5.17 | 105.0 |
| 5.97 | 4 (8a) | 1.85 | 0.26 | 2.83 | 3.63 | 0.50 | 0.12 | 6.36 | 103.0 |
|  | (8b) | 0.01 | — | 0.52 | 0.56 | 0.02 | 0.02 | 0.61 |  |
| 21.08 (9) |  | 4.47 | 1.02 | 10.29 | 13.34 | 1.89 | 0.33 | 21.05 |  |
| results after 4 cycles |  | conv. (%) | sel$_{VA}$ (10) | sel$_{5-FVA}$ | sel$_{FVA}$ | sel$_{dicarboxylic\ acids}$ | sel$_{rest}$ | mass balance | ToF |
|  |  | 78.8 | 6.1 | 62.0 | 80.3 | 11.4 N/Br = 1.9 | 2.1 | 99.9 | 104 |

(1) amount of 3-PA (3-pentenoic acid) added;
(2) amount of pentenoic acid (PA) in ether layer;
(3) amount of valeric acid (VA) in ether layer expressed in grammes of 3-pentenoic acid (gPa);
(4) ditto for 5-formylvaleric acid (5-FVA);
(5) ditto for total of isomeric formylvaleric acids (FVA);
(6) ditto for dicarboxylic acids;
(7) ToF = turn-over frequency = moles of product prepared per mole of platinum per hour;
(8a) composition of ether phase;
(8b) composition of water phase;
(9) results of the total after 4 cycles;
(10) total selectivity (sel) for valeric acid, 5-formylvaleric acid etc. after 4 cycles

What is claimed is:

1. A process to separate linear 5-formylvaleric acid from a mixture of 5- and 3- and/or 4-branched formylvaleric acids, comprising performing the separation by fractional extraction with two immiscible solvents, wherein one solvent is an aqueous solvent and the other solvent is an organic solvent which has the following characteristics:

$-2.8 < A < -0.2$ and $0.14 < B < 2.39$ or $1.7 < A < 4.0$ and $-4.0 < B < -1.64$ in which, A and B are:

$A = 0.23 * (T_B - 138.54)/62.36 +$
$0.24 * (\rho - 935.64)/184.82 +$
$0.0554 * (n_d - 1.4370)/0.0635 +$
$0.3916 * (\epsilon_r - 15.02)/18.66 +$
$0.1208 * (\delta_d - 16.68)/1.738 +$
$0.4135 * (\delta_p - 6.11)/5.16 +$
$0.3462 * (\delta_h - 8.05)/6.97 +$
$0.4177 * (\delta - 20.69)/5.087 +$
$0.3370 * (\mu - 1.73)/1.20 +$
$0.3723 * (E_{T(30)} - 41.14)/7.61$ $B = -0.3009 * (T_B - 138.54)/62.36 -$
$0.3882 * (\rho - 935.64)/184.82 -$
$0.5914 * (n_d - 1.470)/0.0635 +$
$0.1225 * (\epsilon_r - 15.02)/18.66 +$
$0.5506 * (\delta_d - 16.68)/1.738 +$
$0.0970 * (\delta_p - 6.11)/5.16 +$
$0.2291 * (\delta_h - 8.05)/6.97 +$
$0.0583 * (\delta - 20.69)/5.087 +$
$0.0381 * (\mu - 1.73)/1.20 +$
$0.1550 * (E_{T(30)} - 41.14)/7.61$ in which $T_B$ represents the normal boiling point (° C.), $\rho$ the density measured at 20° C. (kg/m$^3$), $n_d$ the refractive index (–), $\epsilon_r$ the di-electric constant measured at 20° C. (–), $\delta_d$ the Hansen solubility parameter of dispersion (Mpa$^{1/2}$), $\delta_p$ the Hansen solubility parameter of polarity (Mpa$^{1/2}$), $\delta_h$ the Hansen solubility parameter of hydrogen bonding (Mpa$^{1/2}$), $\delta$ the Scatchard-Hildebrand Volubility parameter (Mpa$^{1/2}$), $\mu$ the dipole moment (Debey) and $E_{T(30)}$ the Lewis donor/acceptor property (kcal/mol) or the organic solvent is an ether or an ester with 2 to 10 carbon atoms represented by the following formula $$R^1-O-R^2 \qquad (7)$$

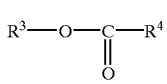

(8)

in which R$^1$, R$^2$, R$^3$ and R$^4$ are independently an alkyl or aryl group with 1 to 7 carbon atoms and in which R$^1$ and R$^2$ is optionally a divalent group.

2. A process according to claim 1, wherein $B < -1.12*A + 0.96$ and $B > 0.965*A - 1.033$.

3. A process according to claims 1 or 2, wherein $-2.8 < A < -0.2$ and $0.14 < B < 2.39$.

4. A process according to claim 1 or 2, wherein the fractional extraction is performed continuously in which initially pure water and initially pure organic solvent are contacted counter currently in various contacting stages in which the crude mixture of formylvaleric acids is continuously fed at an intermediate stage resulting in a water phase rich in 5-formylvaleric acid and an organic phase rich in 3-formylvaleric acid, 4-formylvaleric, or a mixture thereof.

5. A process for the preparation of ∈-caprolactam comprising:

(a) hydroformylating pentenoic acid to a mixture of 5-formylvaleric acid plus at least one of 3-, formylvaleric acid, 4-formylvaleric acid, in an aqueous solution and subsequently separating 5-formylvaleric acid from the 3- and/or 4-formylvaleric acid according to claim 1 or 2.

(b) reductively aminating the 5-formylvaleric acid in the aqueous solution from (a) to obtain an aqueous mixture comprising 6-aminocaproic acid and ∈-caprolactam, (c) cyclizing the 6-aminocaproic acid to ∈-caprolactam at elevated temperature, and (d) separating ∈-caprolactam from the aqueous mixture.

6. A process according to claim 5 wherein (c) is performed using the aqueous mixture obtained in (b).

7. A process for preparing 5-formylvaleric acid comprising:

hydroformylating pentenoic acid to obtain a mixture of 5-formylvaleric acid and at least one of 3-formylvaleric acid or 4-formylvaleric acid, and separating 5-formylvaleric acid from said mixture by the process according to claim 1 or 2.

8. A process according to claim 7, wherein the hydroformylating is conducted in the presence of water and a water soluble catalyst system comprising platinum or a platinum compound and a water soluble organic bidentate ligand.

* * * * *